United States Patent [19]

Caubere et al.

[11] Patent Number: 5,190,671
[45] Date of Patent: Mar. 2, 1993

[54] PROCESS FOR THE SYNTHESIS OF MONOHALOALKANOYLFERROCENES

[75] Inventors: Paul Caubere, Nancy; Yves Fort, Vandoeuvre Les Nancy; Jean-Claude Gautier, Ablon Sur Seine; Jean-Claude Mondet, Vert Le Petit, all of France

[73] Assignee: Societe Nationale Des Poudres Et Explosifs, Paris, France

[21] Appl. No.: 769,776

[22] Filed: Oct. 2, 1991

[30] Foreign Application Priority Data

Oct. 3, 1990 [FR] France ............... 90 12157

[51] Int. Cl.$^5$ .................................. C07F 17/02
[52] U.S. Cl. ..................... 210/767; 210/192; 514/502
[58] Field of Search ............ 210/192, 767, 774; 424/295

[56] References Cited

U.S. PATENT DOCUMENTS

| | | | |
|---|---|---|---|
| 3,099,669 | 7/1963 | Leigh | 260/439 |
| 4,118,509 | 10/1978 | Lattrell et al. | 424/295 |
| 4,141,991 | 2/1979 | Lattrell et al. | 424/295 |

FOREIGN PATENT DOCUMENTS

| | | |
|---|---|---|
| 1161560 | 1/1964 | Fed. Rep. of Germany . |
| 2352825 | 12/1977 | France . |
| 2352826 | 12/1977 | France . |

Primary Examiner—Frank Spear
Attorney, Agent, or Firm—Cushman, Darby & Cushman

[57] ABSTRACT

The present invention relates to a process for the synthesis of monohaloalkanoylferrocenes of general formula (I)

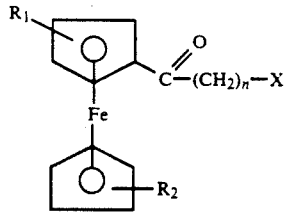

in which $X=Cl$, Br, n is an integer such that $2 \leq n \leq 7$, $R_1$ and $R_2=H$, $C_1-C_8$ alkyl chain. A ferrocene derivative of general formula (II)

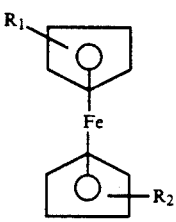

in which $R_1$ and $R_2$ have the abovementioned meaning, is reacted at a temperature $-5° C. < \theta_r < +15° C.$, in the presence of $AlCl_3$ with a halide or the anhydride of an acid of general formula (III) $HOOC-(CH_2)_n-X$, X and n having the abovementioned meaning. An acylating solution obtained by mixing $AlCl_3$ and the acid halide or anhydride in $CH_2Cl_2$, whose temperature $\theta_a$ is such that $5° C. \leq \theta_r - \theta_a \leq 15° C.$, is progressively added to a solution of the ferrocene derivative (II) in $CH_2Cl_2$. The molar ratio of the acid halide or anhydride to the ferrocene derivative is between 0.99 and 1.01 and that of $AlCl_3$ to the ferrocene derivative between 1.05 and 1.11. The mixture is then hydrolyzed and the crude product (I) is recovered by filtration followed by evaporation of $CH_2Cl_2$. This process enables a crude synthetic product to be obtained in a yield and with a purity which are high. The monohaloalkanoylferrocenes (I) are synthesis intermediates in pharmacy and in self-propulsion.

10 Claims, No Drawings

PROCESS FOR THE SYNTHESIS OF MONOHALOALKANOYLFERROCENES

The present invention relates to monohalo-alkanoyl-ferrocenes, and more particularly to 4-chlorobutyroyl-ferrocene. Its subject is a new process for the synthesis of these compounds which are especially synthesis intermediates in fields as diverse as pharmacy and self-propulsion.

French Patent FR 2,259,598 describes, for example, 4-chlorobutyroylferrocene, chloropropionylferrocene,-chloroacetylferrocene, bromopentanoylferrocene and bromohexanoylferrocene as intermediates for the synthesis of ferrocene derivatives employed as medications, in particular as haematic agents.

In the field of self-propulsion, monohaloalkanoylferrocenes are intermediates for the synthesis especially of silylferrocene compounds employed, for example, as combustion catalyst. Patents FR 2,567,890 and FR 2,567,895, to which the Applicant Company holds title, describe, for example and respectively, silylferrocene compounds and ethylenically unsaturated polymers containing silylferrocene groups, employed for this purpose.

However, the use of monohaloalkanoylferrocenes as intermediates in the synthesis of these silylferrocene derivatives is at present very restricted because of the presence of a relatively large quantity of ferrocene and of 1,1'-di(monohaloalkanoyl)ferrocene as impurities in the crude synthetic monohaloalkanoylferrocenes obtained by the conventional Friedel and Crafts process from ferrocene and a carboxylic acid halide or anhydride. Now, residual ferrocene tends to sublime and then deposit on all the cold walls (traps, tubing, etc.) during the subsequent stages, and the presence of 1,1'-di(monohaloalkanoyl)ferrocene results in ferrocene polymers of poor quality because of its difunctionality which gives rise to an untimely crosslinking.

It is furthermore very difficult and costly to purify the crude synthetic monohaloalkanoylferrocenes obtained after the catalyst has been filtered off and the solvent evaporated off.

The specialist is therefore searching for an improvement to the abovementioned Friedel and Crafts process, making it possible to obtain, in a very high yield, a crude synthetic monohaloalkanoylferrocene of very high purity and in particular containing, by weight, less than approximately 3% of 1,1-di(monohaloalkanoyl)-ferrocene and less than approximately 3% of ferrocene.

French Patents FR 2,352,825 and FR 2,352,826 describe the synthesis of 3,5,5-trimethylhexanoylferrocene and of cycloalkenoylferrocenes respectively, by the Friedel and Crafts method by reacting ferrocene with an acid chloride in $CH_2Cl_2$ medium and in the presence of $AlCl_3$ as Catalyst. According to an alternative form, a mixture of acid chloride and of $AlCl_3$ in $CH_2Cl_2$ is poured dropwise into a solution of ferrocene in $CH_2Cl_2$. The reaction temperature is 15° C. and the acid chloride and $AlCl_3$ are present in the same molar quantity (110 mol% relative to ferrocene). The crude synthetic product thus obtained is impure and is subjected to a relatively complex crystallisation treatment followed by washings with methanol and then recovery from the methanol washes to obtain a pure product in a high yield.

The Applicant Company has found that, unexpectedly, a crude synthetic product which has a purity generally in the vicinity of 95%, containing less than 3% of ferrocene and less than 3% of 1,1'-di(monohaloalkanoyl)ferrocene is obtained in a yield which is generally of the order of or higher than 90% by combining operating conditions which are well specified, especially insofar as the temperature, the concentration and the quantity of the reactants are concerned.

The process according to the invention for the synthesis of monohaloalkanoylferrocenes of general formula (I)

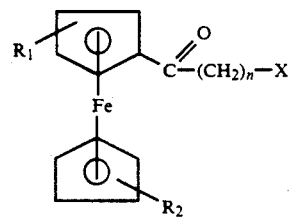

in which X denotes chlorine or bromine, preferably chlorine, n is an integer such that $2 \leq n \leq 7$, preferably such that $3 \leq n \leq 7$, and more particularly $n=3$, $R_1$ and $R_2$, which are identical or different, denote hydrogen or an alkyl chain containing 1 to 8 carbon atoms, is characterised in that a ferrocene derivative of general formula (II)

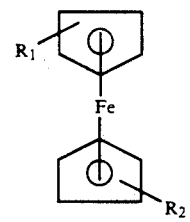

in which $R_1$ and $R_2$ have the abovementioned meaning, is reacted at a temperature $\theta_r$ of between $-5°$ C. and $+15°$ C., preferably in the vicinity of 0° C., in the presence of aluminum chloride as catalyst, with a halide or the anhydride, preferably the chloride, of an acid of general formula (III) $HOOC(-O-CH_2)_n-X$, X and n having the above-mentioned meaning.

To carry out this reaction an acylating solution is prepared first of all by mixing $AlCl_3$ and the halide or the anhydride of the acid (III), in methylene chloride. The temperature $\theta_n$ of this acylating solution is lower than $\theta_r$ so that $5° C. \leq \theta_r - \theta_a \leq 15°$ C.

The concentration of the acid halide or anhydride is preferably higher than 0.9 M.

This acylating solution is gradually added to a solution at a concentration which is preferably between 0.25 and 0.6 M, for example in the vicinity of 0.5 M, of the ferrocene derivative (II) in methylene chloride.

The molar ratio of the halide or anhydride of the acid (III) to the ferrocene derivative (II) is between 0.99 and 1.01 and the molar ratio of aluminum chloride to the ferrocene derivative (II) is between 1.05 and 1.11, preferably in the vicinity of 1.10.

The reaction mixture is then hydrolysed to recover an organic phase and the required product of formula (I) is then recovered by filtering this organic phase to remove the aluminum chloride in suspension, followed by evaporation of the methylene chloride, for example at reduced pressure and/or with slight heating.

$R_1$ and $R_2$, which are identical or different, preferably denote hydrogen, a methyl chain or an ethyl chain. In a particularly preferred manner $R_1$ and $R_2$ denote hydrogen. According to this latter alternative form, special preference is given to 4-chlorobutyroylferrocene in the case of which X denotes chlorine and n=3.

According to another preferred alternative form of the process according to the invention $\theta_r - \theta_a$ is in the vicinity of 10° C.

The period of addition of the acylating solution is generally between 0.5 h and 5 h, preferably between 1 h and 3 h.

Furthermore, the Applicant Company has found that when the solution of the ferrocene derivative (II) in $CH_2Cl_2$ also contains a cerous salt, especially a halide and more particularly the chloride, the residual ferrocene content is considerably decreased and that it is possible in this way, without loss of yield, to obtain a crude reaction product which has a purity in the vicinity of 98%. The result is particularly unexpected since cerous salts, just like ferrocene, are reducing agents, and no explanation has been found.

The cerous salt is preferably present at between 1 and 15 mol% in relation to the ferrocene derivative (II).

The following nonlimiting examples illustrate the invention and the advantages which it provides.

EXAMPLES 1 to 4

Synthesis according to the invention of 4-chlorobutyroylferrocene

EXAMPLE 1 a) Preparation of the acylating solution 7 37 g (55 mmol) of $AlCl_3$ in suspension in 20 ml of $CH_2Cl_2$ at room temperature (approximately 20° C.) and under nitrogen atmosphere are placed in a reactor fitted with a condenser, a dropping funnel and a thermometer.

A solution of 7.05 g (50 mmol) of 4-chlorobutyroyl chloride in 20 ml of $CH_2Cl_2$ is then added dropwise over approximately 30 min by means of the dropping funnel.

The suspension is stirred at room temperature for 2 h.

After this period all the aluminum chloride has dissolved and the solution obtained, light-yellow in colour, is clear.

b) Addition of the acylating solution to ferrocene

The acylating solution, precooled to $\theta_a = -10°$ C., is added gradually by means of a transfer line connected to a pump, to a reactor under nitrogen containing 9.30 g of ferrocene (50 mmol) in solution in 120 ml of $CH_2Cl_2$ at 0° C. ($\theta_r$). The period of addition of the acylating solution is 2.5 h. The reaction mixture is then allowed to return to room temperature.

c) Hydrolysis and recovery of the crude product

The reaction mixture is then poured onto 500 g of ice. The organic phase is recovered and the aqueous phase is then extracted twice with 150 ml of $CH_2Cl_2$. The organic phases are combined. They are washed twice with a saturated aqueous solution of $NaHCO_3$ and are then dried over $MgSO_4$.

After filtration and then evaporation of methylene chloride, crude synthetic 4-chlorobutyroylferrocene was obtained in a 93.8% yield based on the initial ferrocene.

This isolated crude 4-chlorobutyroylferrocene has a purity of 96% and contains, by weight, 2% of ferrocene and 2% of 1,1'-di(4-chlorobutyroyl)ferrocene (determinations carried out by gas phase chromatography and by high-pressure liquid chromatography).

EXAMPLE 2

The procedure is the same as in Example 1, but the solution of ferrocene in methylene chloride contains 1.23 g of cerous chloride (5 mmol).

Crude 4-chlorobutyroylferrocene is obtained in a 93.2% yield. Its purity is 97.7% and it contains, by weight, 0.4% of ferrocene and 1.9% of 1,1'-di(4-chlorobutyroyl)ferrocene.

EXAMPLES 3 and 4

The procedure is the same as in Example 1 but 52.5 mmol of $AlCl_3$ are employed in the case of Example 3 and 54 mmol of $AlCl_3$ in the case of Example 4, instead of 55 mmol.

The crude isolated 4-chlorobutyroylferrocene contains 2.5% of ferrocene and 2.2% of 1,1'-di(4-chlorobutyroyl)ferrocene in the case of Example 3 (95.3% purity) and 3.4% of ferrocene and 2.7% of 1,1'-di(4-chlorobutyroyl)ferrocene in the case of Example 4 (94% purity).

The yields are 91% and 89% respectively.

EXAMPLES 5 to 13

Synthesis of 4-chlorobutyroylferrocene. Comparative tests

These comparative tests do not form part of the invention and are intended to show that the choice of parameters according to the invention is not arbitrary and that it is needed to obtain the technical effect which makes it possible to solve the abovementioned problem.

COMPARATIVE EXAMPLES 5 to 9

Influence of the quantity of $AlCl_3$ and of the acid chloride in relation to ferrocene The procedure is the same as in Example 1 according to the invention, but the quantities of $AlCl_3$ and/or of the acid chloride are modified so a to obtain the following ferrocene/acid chloride/$AlCl_3$ molar ratios respectively:

EXAMPLE 5

1.00/1.00/1.12

EXAMPLE 6

1.00/1.00/1.15

EXAMPLE 7

1.00/0.90/1.10

EXAMPLE 8

1.00/0.95/1.045

EXAMPLE 9

1.00/1.10/1.20 the yield an the purity of the crude 4-chlorobutyroylferrocene isolated are detailed in Table 2 below for each of these examples, in comparison with Example 1 according to the invention.

| EX | YIELD (%) | PURITY (% BY WEIGHT) | RESIDUAL FERROCENE (% BY WEIGHT) | RESIDUAL 1,1'-DI(4-CHLORO-BUTYROYL) FERROCENE (% BY WEIGHT) |
|---|---|---|---|---|
| 1 | 93.8 | 96 | 2.0 | 2.0 |
| 5 | 85.4 | 91 | 4.3 | 4.6 |
| 6 | 84.1 | 88.5 | 4.6 | 6.8 |
| 7 | 93.6 | 90.3 | 8.4 | 1.3 |
| 8 | 87.6 | 92.5 | 6.1 | 1.4 |
| 9 | 77.9 | 85 | 0.8 | 14.1 |

COMPARATIVE EXAMPLES 10 to 13

Influence of the reaction temperature $\theta_r$ and/or of the acylating solution temperature $\theta_a$ The procedure is the same as in Example 1 according to the invention but with $\theta_r$ and/or $\theta_a$ modified as follows:

EXAMPLE 10

$\theta_r = \theta_a$ = room temperature, in the vicinity of 20° C.

EXAMPLE 11

$\theta_r = \theta_a = -25°$ C.

The yield and the purity of the crude 4-chlorobutyroylferrocene isolated are detailed in Table 2 below for each of these examples, in comparison with Example 1 according to the invention.

| EX | YIELD (%) | PURITY (% BY WEIGHT) | RESIDUAL FERROCENE (% BY WEIGHT) | RESIDUAL BIS(4-CHLORO-BUTYROYL) FERROCENE (% BY WEIGHT) |
|---|---|---|---|---|
| 1 | 93.8 | 96 | 2.0 | 2.0 |
| 10 | 84.3 | 90 | 3.0 | 7.0 |
| 11 | 85.1 | 90 | 4.0 | 6.1 |
| 12 | 86.1 | 92 | 4.0 | 4.0 |
| 13 | 85.1 | 93 | 7.1 | 0.0 |

EXAMPLE 14

Synthesis of ethyl-4-chlorobutyroylferrocene

The operating conditions of Example 1 are followed, using 50 mmol of ethylferrocene instead of 50 mmol of ferrocene. A crude synthetic product is obtained, consisting of a mixture of isomers of ethyl-4-chlorobutyroylferrocene.

The crude product, obtained in an 89% yield, contains 1% by weight of ethylferrocene and 3% by weight of 1,1'-di(4-chlorobutyroyl)ethylferrocene.

We claim:

1. Process for the synthesis of monohaloalkanoylferrocenes of general formula (I)

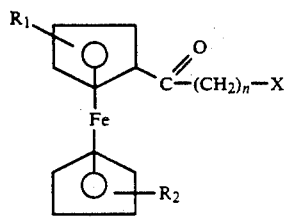

in which

X denotes chlorine or bromine, n is an integer such that $2 \leq n \leq 7$, $R_1$ and $R_2$, which are identical or different, denote hydrogen or an alkyl chain containing 1 to 8 carbon atoms, characterised in that a ferrocene derivative of general formula (II)

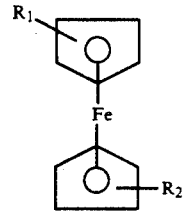

in which $R_1$ and $R_2$ have the abovementioned meaning, is reacted at a temperature $\theta_r$ of between $-5°$ C. and $+15°$ C., in the presence of aluminum chloride as catalyst, with a halide or the anhydride of an acid of general formula (III) HOOC—$(CH_2)_n$—X, X and n having the abovementioned meaning, an acylating solution obtained by mixing $AlCl_3$ and the halide or the anhydride of acid (III) in methylene chloride and whose temperature $\theta_a$, lower than $\theta_r$, is such that $5°$ C.$\theta_r - \theta_a \leq 15°$ C., being progressively added to a solution of the ferrocene derivative (II) in methylene chloride, the molar ratio of the acid halide or anhydride to the ferrocene derivative being between 0.99 and 1.01 and the molar ratio of aluminum chloride to the ferrocene derivative being between 1.05 and 1.11, in that the reaction mixture is then hydrolysed to recover an organic phase, and in that the required product of formula (I) is recovered by filtering this organic phase and then evaporating off methylene chloride.

2. Process according to claim 1, characterised in that the concentration of the halide or the anhydride of the acid (III) in the acylating solution is higher than 0.9 M and in that the concentration of the ferrocene derivative (II) in $CH_2Cl_2$ is between 0.25 M and 0.6

3. Process according to either of claims 1 and 2, characterised in that $R_1$ and $R_2$, which are identical or different, denote hydrogen, a methyl chain or an ethyl chain.

4. Process according to claim 1 characterised in that the acid halide or anhydride is an acid chloride.

5. Process according to claim 1 claims, characterised in that X denotes chlorine.

6. Process according claim 1 claims, characterised in that $R_1$ and $R_2$ denote hydrogen, X denotes chlorine and in that n is equal to 3.

7. Process according to claim 1 claims, characterised in that the reaction temperature is 0° C., the molar ratio of the acid halide or anhydride to the ferrocene derivative is 1.00 and the molar ratio of aluminum chloride to the ferrocene derivative is 1.10.

8. Process according to claim 1 claims, characterised in that the addition period of the acylating solution is between 1 h and 3 h.

9. Process according to claim 1 claims, characterised in that the solution of the ferrocene derivative (II) in methylene chloride contains a cerous salt, preferably cerous chloride.

10. Process according to claim 9, characterised in that the cerous salt is present at between 1 and 15 mol% in relation to the ferrocene derivative (II)

* * * * *